United States Patent [19]

Mentrup et al.

[11] 4,341,778
[45] Jul. 27, 1982

[54] 3,1 BENZOXAZIN-2-ONES AND USE THEREOF

[75] Inventors: Anton Mentrup, Mainz-Kastel; Kurt Schromm; Ernst-Otto Renth, both of Ingelheim; Wolfgang Hoefke, Wiesbaden; Wolfram Gaida, Ingelheim; Ilse Streller, Stromberg; Armin Fügner, Gau-Algesheim, all of Fed. Rep. of Germany

[73] Assignee: C. H. Boehringer Sohn, Ingelheim, Fed. Rep. of Germany

[21] Appl. No.: 280,349

[22] Filed: Jul. 6, 1981

[30] Foreign Application Priority Data

Jul. 12, 1980 [DE] Fed. Rep. of Germany ....... 3026534

[51] Int. Cl.³ .................... A61K 43/86; C07D 265/18
[52] U.S. Cl. ............................ 424/248.5; 424/248.52; 424/248.54; 424/248.55; 424/248.56; 544/92; 544/95
[58] Field of Search ................. 544/92, 95; 424/248.5, 424/248.52, 248.54–248.56

[56] References Cited

U.S. PATENT DOCUMENTS 3,526,621 9/1970 Bernardi et al. ...................... 544/92

Primary Examiner—Richard Raymond
Attorney, Agent, or Firm—Hammond & Littell, Weissenberger & Muserlian

[57] ABSTRACT

The invention relates to compounds of general formula I

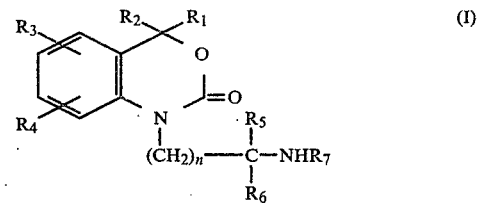

(wherein
$R_1$ and $R_2$, which may be the same or different, each represents a hydrogen atom or a ($C_1$–$C_4$) alkyl group;
$R_3$ and $R_4$, which may be the same or different, each represents a hydrogen, fluorine or chlorine atom or a hydroxy, methyl, ethyl or ($C_1$–$C_4$) alkoxy group, or $R_3$ together with $R_4$ represents a methylenedioxy group;
$R_5$ and $R_6$, which may be the same or different, each represents a hydrogen atom or a methyl group;
$R_7$ represents a group of formula

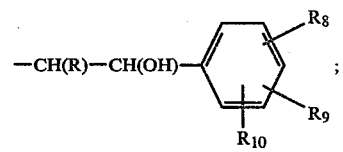

R represents a hydrogen atom or a ($C_1$–$C_4$) alkyl group;
$R_8$ represents a fluorine or chlorine atom or a ($C_1$–$C_4$) alkyl, ($C_1$–$C_4$) alkylthio, hydroxymethyl, $CONHR_{11}$, $SO_2NHR_{11}$, $OR_{12}$, methoxycarbonyl, ethoxycarbonyl or $NHSO_2CH_3$ group;
$R_9$ represents a hydrogen, fluorine or chlorine atom or a $OR_{12}$ group;
$R_{10}$ represents a hydrogen or chlorine atom or an amino, methyl or methoxy group;
$R_{11}$ represents a hydrogen atom or a methyl, ethyl or hydroxyethyl group;
$R_{12}$ represents a hydrogen atom or a ($C_1$–$C_4$) alkyl, ($C_1$–$C_4$) alkyl-CO, aryl-$CH_2$ or aryl-CO group; and
n represents 1, 2 or 3) and acid addition salts thereof as well as to processes for their preparation and pharmaceutical compositions containing them. The compounds of the invention possess interesting pharmacological properties in particular displaying hypotensive and selective tocolytic effects.

5 Claims, No Drawings

3,1 BENZOXAZIN-2-ONES AND USE THEREOF

The invention relates to 3,1-benzoxazin-2-ones, to processes for their preparation, to pharmaceutical compositions containing them and to their pharmacological use.

It has been found that certain 3,1-benzoxazin-2-ones have interesting pharmacological properties, particularly hypotensive and selective tocolytic effects.

According to one aspect of the present invention we therefore provide compounds of general formula I

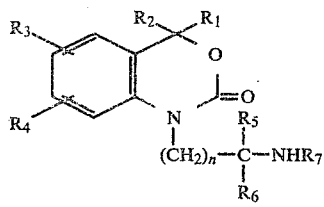

(wherein
$R_1$ and $R_2$, which may be the same or different, each represents a hydrogen atom or a $(C_1-C_4)$ alkyl group;
$R_3$ and $R_4$, which may be the same or different, each represents a hydrogen, fluorine or chlorine atom or a hydroxy, methyl, ethyl or $(C_1-C_4)$ alkoxy group, or $R_3$ together with $R_4$ represents a methylenedioxy group;
$R_5$ and $R_6$, which may be the same or different, each represents a hydrogen atom or a methyl group;
$R_7$ represents a group of formula

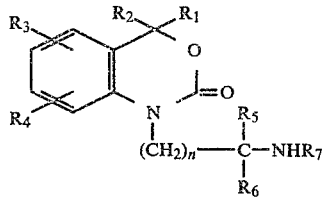

R represents a hydrogen atom or a $(C_1-C_4)$ alkyl group;
$R_8$ represents a fluorine or chlorine atom or a $(C_1-C_4)$ alkyl, $(C_1-C_4)$ alkylthio, hydroxymethyl, $CONHR_{11}$, $SO_2NHR_{11}$, $OR_{12}$, methoxycarbonyl, ethoxycarbonyl or $NHSO_2CH_3$ group;
$R_9$ represents a hydrogen, fluorine or chlorine atom or a $OR_{12}$ group;
$R_{11}$ represents a hydrogen atom or a methyl, ethyl or hydroxyethyl group;
$R_{12}$ represents a hydrogen atom or a $(C_1-C_4)$ alkyl, $(C_1-C_4)$ alkyl-CO, aryl-$CH_2$ or aryl-CO group; and
n represents 1, 2 or 3 and acid addition salts thereof.

If in the compounds of formula I the substituents represent or contain an alkyl group, these may be straight-chained or branched, i.e. a $C_1-C_4$ alkyl substituent group may be a methyl, ethyl, n-propyl, isopropyl, n-butyl, isobutyl, sec.butyl or tert.-butyl group. As "aryl" substituent groups are particularly preferred optionally substituted phenyl groups.

Within the scope of the above definitions, the substituent groups in the compounds of formula I preferably take the following identities:

| | |
|---|---|
| $R_1/R_2$: | $CH_3/CH_3$ or $CH_3/H$; |
| $R_3$: | H, OH or $OCH_3$; |
| $R_4$: | H, |
| $R_5/R_6$: | $CH_3/CH_3$, $CH_3/H$ or H/H; |
| $R_7$: | as hereinbefore defined; |
| R: | H, $CH_3$ or $C_2H_5$; |
| $R_8$: | $CONHR_{11}$, $SO_2NHR_{11}$, $NHSO_2CH_3$, $OR_{12}$, F, Cl, $COOCH_3$, $COOC_2H_5$, or $CH_2OH$; |
| $R_9$: | $OR_{12}$, F, Cl or H; |
| $R_{10}$: | H, $NH_2$, $CH_3$, $OCH_3$ or Cl; |
| $R_{11}$: | H, $CH_3$ or $C_2H_5$; |
| $R_{12}$: | H, aryl—$CH_2$ or $(C_1-C_4)$ alkyl—CO; |
| n: | 1 or 2. |

The compounds according to the invention may possess one or more centres of asymmetry and so may occur in the form of racemates, in the form of diastereoisomers and in the form of the individual enantiomers, either as free bases or as acid addition salts, all of which are deemed to fall within the scope of the invention.

As acid addition salts of compounds of formula I, physiologically acceptable acid addition salts are preferred. However other acid addition salts may be useful in the preparation of physiologically acceptable acid addition salts or of the free base of formula I and so also are considered to fall within the scope of the invention.

According to a further aspect of the present invention we provide a process for the preparation of compounds of general formula I and acid addition salts thereof, which process comprises one or more steps selected from the following:

(a) reducing a compound of general formula II

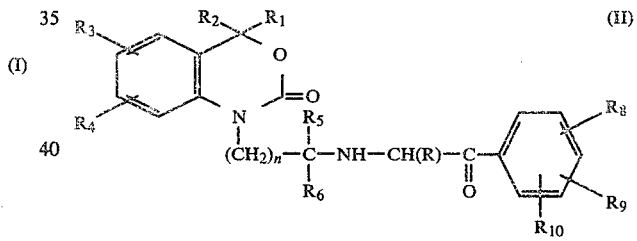

(wherein R, $R_1$, $R_2$, $R_3$, $R_4$, $R_5$, $R_6$, $R_8$, $R_9$, $R_{10}$ and n are as hereinbefore defined);

(b) reductively alkylating an amino compound of general formula III

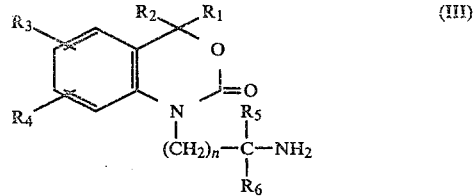

(wherein n, $R_1$, $R_2$, $R_3$, $R_4$, $R_5$ and $R_6$ are as hereinbefore defined) with a compound of general formula IV

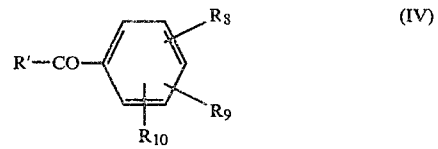

(wherein $R_8$, $R_9$ and $R_{10}$ are as hereinbefore defined and R' represents a group of formula Va or Vb,

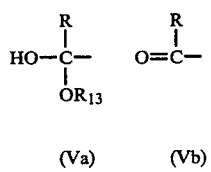

(Va)    (Vb)

in which $R_{13}$ represents a $(C_1-C_4)$ alkyl group);

(c) (for the preparation of compounds of formula I wherein $R_9$ represents -OH) removing the protecting group $R_{14}$ from a compound of general formula VII

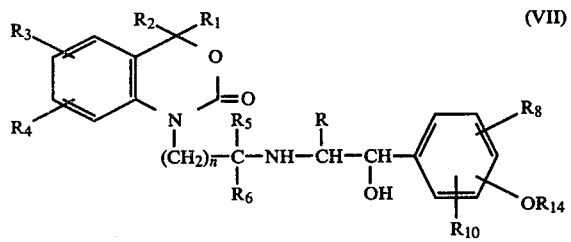

(VII)

(wherein n, R, $R_1$, $R_2$, $R_3$, $R_4$, $R_5$, $R_6$, $R_8$ and $R_{10}$ are as hereinbefore defined and $R_{14}$ represents an optionally substituted benzyl, CO—$(C_1-C_4)$—alkyl or CO-aryl group);

(d) (for the preparation of compounds of formula I wherein $R_8$ represents $CONHR_{11}$) reacting a compound of general formula IX

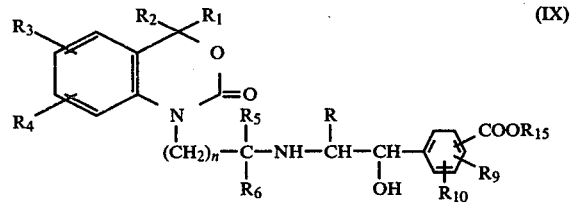

(IX)

(wherein n, R, $R_1$, $R_2$, $R_3$, $R_4$, $R_5$, $R_6$, $R_9$ and $R_{10}$ are as hereinbefore defined and $R_{15}$ represents an optionally substituted alkyl or aralkyl group, preferably a $C_1-C_4$ alkyl group) with an amine of general formula X $H_2NR_{11}$ (X)

(wherein $R_{11}$ is as hereinbefore defined);

(e) converting a compound of formula I into an acid addition salt thereof or an acid addition salt of a compound of formula I into the free base; and (f) separating a mixture of stereoisomers of a compound of formula I or an acid addition salt thereof into its enantiomers or diastereoisomers, for example by conventional racemate resolving techniques such as fractional crystallization.

In process step (a) above, the reducing agents used are preferably complex hydrides, particularly sodium borohydride or hydrogen/hydrogenation catalysts. Examples of such catalysts include, in particular, platinum, palladium and nickel.

Complex hydrides, preferably sodium borohydride or sodium cyanoborohydride, may be used as reducing agents in process step (b) above for the reductive alkylation or the catalytic hydrogenation, preferably with the catalysts platinum, palladium or nickel.

When in process step (b) the amines of formula III and the hemiacetals or carbon compounds of formula IV are combined, Schiff's bases of formula VI

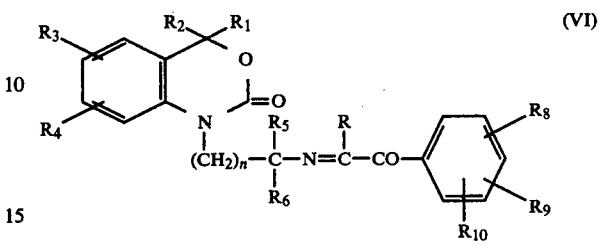

(VI)

may be wholly or partially formed as an intermediate. The reduction of process step (b) above using the reducing agents mentioned above is effected irrespective of whether and to what extent these Schiff's bases are formed.

In process step (c) above, where compounds of formula VII wherein $R_8$ represents $OCH_2$aryl or OCO alkyl are used as starting materials, these groups may also be split off at the same time in which case $R_8$ in the product of formula I will also represent an OH group.

The compounds obtained according to process step (c) above correspond to those of general formula VIII

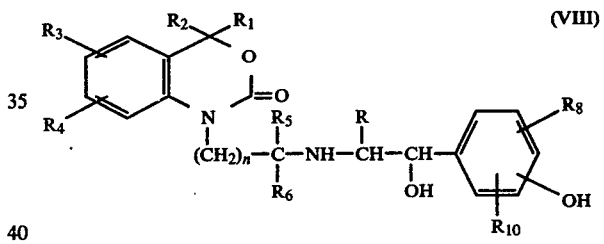

(VIII)

The benzyl protecting group $R_{14}$ may be split off in process step (c) above by catalytic hydrogenation, preferably using one of the catalysts platinum, palladium or nickel. Acyl protecting groups may be removed by saponification with dilute acids or dilute alkaline solutions, e.g. dilute sodium hydroxide solution.

Compounds of general formula XI

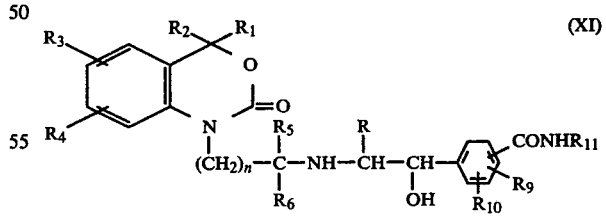

(XI)

are formed by process step (d) above.

The 3,1-benzoxazin-2-ones of formula I according to the invention may be converted, for example in the conventional way, into their acid addition salts, preferably the physiologically acceptable acid addition salts. Suitable acids for the preparation of such salts include, for example, methanesulphonic acid, formic acid, hydrochloric acid, p-aminobenzoic acid, fumaric acid, succinic acid and maleic acid.

PREPARATION OF THE INTERMEDIATE PRODUCTS

The intermediate compounds of general formula XII:

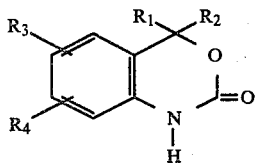
(XII)

are known from the literature or may be prepared according to the processes described for the preparation of the known compounds. They may be prepared, starting from the corresponding substituted anthranilic acid esters XIII by a reaction with a Grignard reagent of formula $R_1MgX$ (wherein X represents a chlorine, bromine or iodine atom):

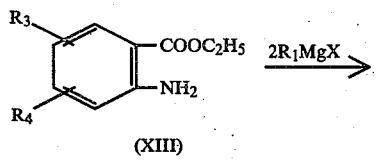
(XIII)

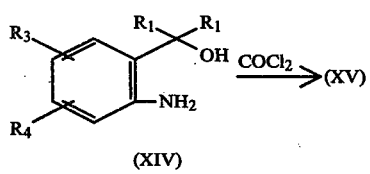
(XIV)

to form the carbinols thereof, of general formula XIV, which are then converted, by reacting with phosgene or chloroformates, into the 3,1-benzoxazin-2-ones of general formula XII in which $R_1$ and $R_2$ represent alkyl groups.

In order to prepare a 3,1-benzoxazin-2-one of general formula XV

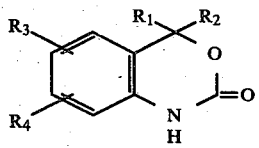
(XV)

(wherein $R_1$ and $R_2$ are identical or different alkyl groups) an o-aminoacetophenone derivative of general formula XVI is reacted with a Grignard reagent of formula $R_2 MgX$ and then with phosgene or a chloroformate to form a 3,1-benzoxazin-2-one of general formula XV.

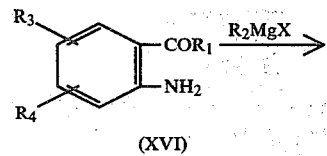
(XVI)

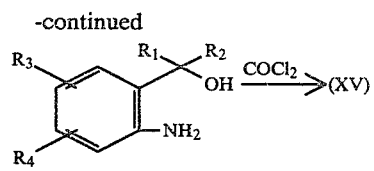

The intermediate compounds of formula XVII:

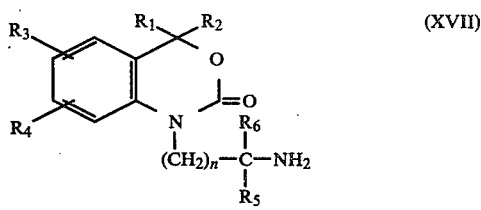
(XVII)

may be prepared by reacting 3,1-benzoxazin-2-ones of general formula XII or XV with compounds of general formula XVIII in the presence of sodium hydride, with the subsequent hydrolysis of the reaction product of general formula XIX:

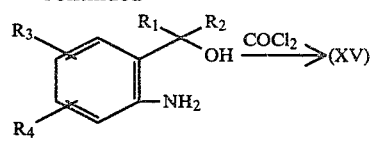

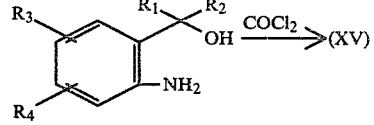

(XIX)

(wherein Y represents a chlorine atom or a group of formula $-OSO_2CH_3$ or $OSO_2C_6H_4CH_3$)

The compounds of general formula II are prepared, starting from the compounds of formula XVII, by reacting with bromoketones of general formula XX (XVII) +

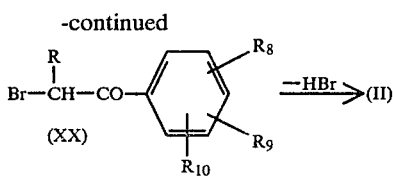

Excess amine of general formula XVII or alkali, such as e.g. soda or potassium bicarbonate, is used as the binder for the hydrogen bromide formed during the reaction.

Aminoketones of general formulae XXI, XXII and XXIII:

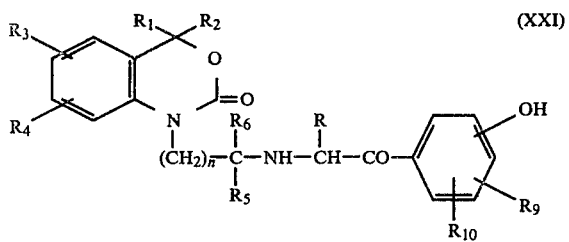

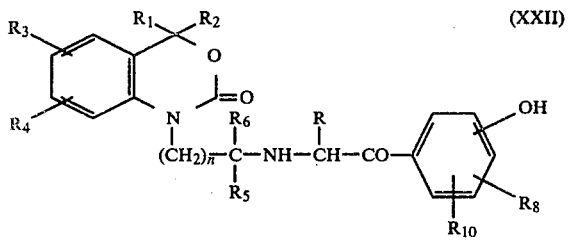

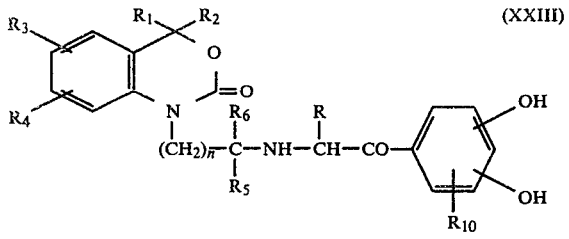

may be prepared from the compounds of general formula XXIV, XXV and XXVI:

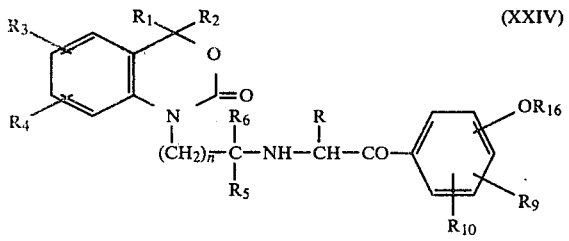

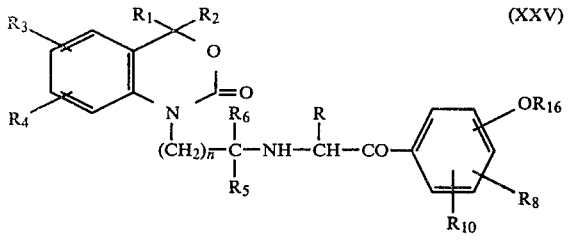

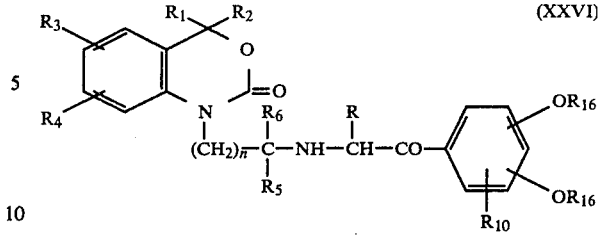

(wherein $R_{16}$ represents a $CH_2C_6H_5$ or $CO$—$(C_1$-$C_4)$ alkyl group) by splitting off the protecting group $R_{16}$.

When $R_{16}$ represents $CH_2C_6H_5$, this protecting group $R_{16}$ may be split off by catalytic hydrogenation with platinum, palladium or Raney nickel as catalyst. If $R_{16}$ represents the $CO$—$(C_1$-$C_4)$ alkyl group, the protecting group may be split off by saponification, particularly in the presence of an acid such as dilute hydrochloric acid.

The compounds of formula I and the polysiologically acceptable acid addition salts thereof have valuable pharmacological properties and are useful in the production of pharmaceutical compositions. Compounds of the invention which have been tested have exhibited favourable hypotensive effects and very active and selective tocolytic effects.

The compounds of the invention may also be useful as broncholytics, vasodilators and cardiac agents. The long duration of activity is also important.

For use, the compounds of formula I or their physiologically acceptable acid addition salts may be processed with excipients conventionally used in galenic pharmacy, to form pharmaceutical compositions according to the invention such as tablets, coated tablets, capsules, tinctures, injection solutions, suppositories, powders for inhalation and metered aerosols.

According to a further aspect of the present invention we provide a pharmaceutical composition comprising as an active ingredient at least one compound of formula I or physiologically acceptable acid addition salt thereof together with a harmaceutical carrier and/or excipient, and preferably in dosage unit form. The compositions of the invention are preferably in forms suitable for oral, rectal or parenteral administration.

According to a yet further aspect of the present invention we provide a method of treatment of the human or animal body to achieve a hypotensive, tocolytic, broncholytic, vasodilatory or cardiac effect, the said method comprising administering to the said body an effective quantity of at least one compound of formula I or physiologically acceptable acid addition salt thereof, advantageously in the form of a pharmaceutical composition according to the invention.

The dosage of the new compounds varies, depending on the indication, the method of administration and the substance used, as well as the body weight of the patient to be treated. For use as a hypotensive agent in adults, the oral dose is suitably between 5 and 2000 mg, preferably between 20 and 1000 mg. For use as tocolytics, it is advantageous to use tablets which contain 0.1 to 50 mg, preferably 0.5 to 20 mg, of active substance, or ampoules containing 0.1 to 10 mg, preferably 0.2 to 2 mg, of active substance.

The hypotensive effect of the compounds and salts according to the invention was determined using the method described hereinafter:

The blood pressure (mean pressure) of conscious male rats with congenital hypertension (SH rats of the OKAMOTO and AOKI strain) was recorded with Statham pressure transducers on a compensation recorder by means of a catheter chronically implanted in the aorta by the method of WEEKS. The cardiac frequency was calculated from the number of pulse waves. The test substance was administered orally, after a preliminary period of 1 hour, to the animals which were able to move freely and had been familiarised with the method. The blood pressure and cardiac frequency were then recorded for a period of 6 hours. If, at the end of this period, the starting value for the blood pressure and/or cardiac frequency had not been even approximately regained, further measurements were carried out on the following day.

The test substance was administered orally by oesophageal tube, as a suspension of the solution in a 1% aqueous Tylose solution. The doses administered were 10 mg/kg. (Literature: OKAMOTO, K. and K. AOKI: Jap. Circul. J. 87, 2821 (1963) WEEKS, J. R. and J. A. JONES: Proc. Soc. Exp. Biol. Med. 104, 646 (1960)).

Using this method, the effect on blood pressure (RR; values in mbar) and cardiac frequency (HF; beats per minute) was determined, for example, for 1-(3-methyl carbamoyl-4-hydroxyphenyl)-2-{1,1-dimethyl-3-[1-(4,4-dimethyl-3,1-benzoxazin-2-onyl)]-propylamino}-ethanol-methanesulfonate, by repeated oral administration to rats with congenital hypertension:

|  | Starting value | Value after 6 hours |  |
|---|---|---|---|
| 1st day Dosage |  |  |  |
| 10 mg/kg | 274 | 248 | RR |
|  | 389 | 390 | HF |
| 2nd day Dosage |  |  |  |
| 10 mg/kg | 238 | 226 | RR |
|  | 384 | 345 | HF |
| 3rd day Dosage |  |  |  |
| 10 mg/kg | 214 | 202 | RR |
|  | 320 | 360 | HF |
| 4th day 1 ml/kg NaCl 0.9% | 217 | 228 | RR |
|  | 336 | 328 | HF |
| 5th day 1 ml/kg NaCl 0.9% | 252 | 266 | RR |
|  | 350 | 325 | HF |

As the table shows, the blood pressure falls to a level below the starting value after each dosage on the first three days. On the following days, the blood pressure rises only slowly to a level approaching the starting value. The $LD_{50}$ of the above-mentioned compound is >1500 mg/kg (p.o. in the rat).

The following results obtained with 1-(3-methane-sulfonamido-4-hydroxyphenyl)-2-{1,1-dimethyl-3-[1-(4-methyl-3,1-benzoxazin-2-onyl)]-propylamino}-ethanol illustrate the tocolytic effect of the compounds according to the invention.

When administered intravenously in a dosage of 0.035 μg/kg to rats drugged with urethane, the above compound leads to a reduction in the amplitude of uterine contractions of more than 10%, over a period of 8 minutes, in 50% of the test animals. At this dosage, an increase in cardiac frequency of 2 beats per minute is observed, lasting 6 minutes. In addition, the frequency of uterine contractions was included in the assessment. For this, the product of the amplitude and frequency for periods of 5 minutes was determined; the starting value was taken as 100%. A dosage of 0.09 μg/kg i.v. resulted in a 50% reduction in this value, lasting for a period of 14 minutes. This dosage leads to an increase in cardiac frequency of 2 beats per minute, leasting for a period of 6 minutes.

The following Examples are provided to illustrate the invention without serving to restrict the scope of protection sought therefor:

(EXAMPLES RELATING TO PROCESS STEP (A))

EXAMPLE 1

1-(3-Methylcarbamoyl-4-hydroxyphenyl)-2-{1,1-dimethyl-3-[1-(4,4-dimethyl-3,1-benzoxazin-2-onyl)]-propylamino}-ethanol

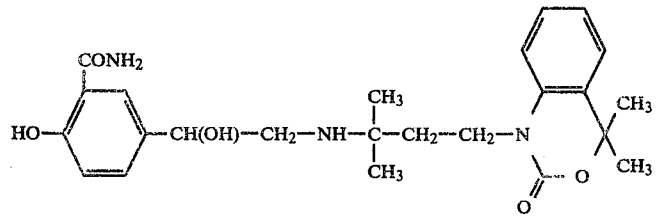

A mixture of 2.6 g of 3-carbamoyl-4-hydroxy-α-bromoacetophenone and 2.6 g of 1,1-dimethyl-3-[1-(4,4-dimethyl-3,1-benzoxazin-2-onyl)]-propylamine is refluxed in 50 ml of ethyl acetate for 25 minutes. Whilst still warm, the solution is suction filtered to remove the precipitated amine hydrobromide, the filtrate is cooled, diluted with 10 ml of ethanol and mixed with 0.2 g of sodium borohydride at 0° C. The solution, kept at a temperature of 0° to 10° C., is stirred for 2 hours, then acidified with 8 ml of 50% acetic acid. After the solvent has been distilled off in vacuo, the residue is mixed with a solution of 1.4 g of potassium carbonate in 7 ml of water and the mixture is extracted three times with ethyl acetate. The ethyl acetate phase is dried over sodium sulphate and concentrated by evaporation until the title compound starts to crystallise out. 1.1 g of substance are obtained which, after recrystallisation, has a melting point of 197° C. The methanesulphonate (m.p. 138° C.) is obtained by the addition of methanesulphonic acid in acetonitrile.

EXAMPLE 2

1-(3-Methanesulfonamido-4-hydroxyphenyl)-2-{1,1-dimethyl-3-[1-(4,4-dimethyl-3,1-benzoxazin-2-onyl)]-propylamino}-ethanol

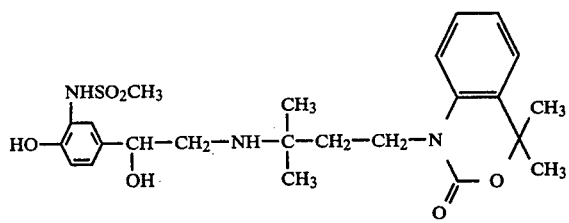

A mixture of 4.0 g of 3-methanesulfonamido-4-benzoyloxy-α-bromoacetophenone and 5.2 g of 1,1-dimethyl-3-[1-(4,4-dimethyl-3,1-benzoxazin-2-onyl)]-propylamine is refluxed for 30 minutes in 100 ml of ethylacetate. After cooling, the precipitated amine hydrobromide is suction filtered and the filtrate is concentrated by evaporation. 5.5 g of the reaction product (in the form of the hydrochloride, m.p. 205° C.) are dissolved in 120 ml of methanol and, in order to remove the benzyl group, hydrogenated at ambient temperature and under normal pressure with Pd/C until 230 ml of hydrogen have been absorbed. After removal of the catalyst, all the methanol is distilled off in vacuo and the ketone formed is dissolved in acetonitrile. The hydrochloride (m.p. 257° C.) is obtained by the addition of ethereal hydrochloric acid. 2 g of this substance are hydrogenated in 200 ml of methanol at ambient temperature and under normal pressure with 0.2 g of platinum oxide as catalyst, until 84 ml of hydrogen have been absorbed. The resulting product is the title compound which is isolated as a base (m.p. 192° C.) in a yield of 90% of theory.

The following were obtained analogously to Examples 1 and 2 by process step (a):

-continued
| Example | Compound | Characteristics |
|---|---|---|
| 7 | 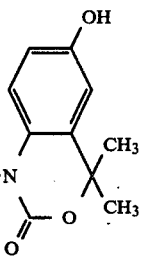 | Mp. Base: 176° C.<br>Mp. Salt: 181° C.<br>Formate |
| 8 | 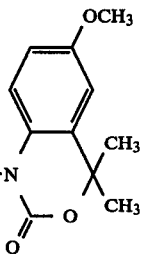 | Mp. Salt: 210° C.<br>Hydrochloride |
| 9 | 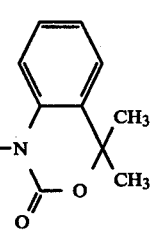 | Mp. Salt: 165° C.<br>p-Aminobenzoate |
| 10 | 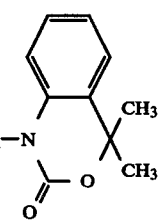 | Mp. Salt: 164° C.<br>Formate |
| 11 | 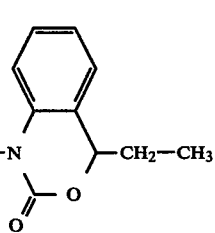 | Mp. Base: 163° C.<br>Mp. Salt: 181° C.<br>Hydrochloride |
| 12 | 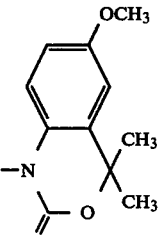 | Mp. Base: 181° C.<br>Mp. Salt: 183° C.<br>Hydrochloride |

-continued

| Example | Compound | Characteristics |
|---|---|---|
| 13 | CH₃—SO₂—NH–[2-OH,5-(CH(OH)CH₂NH–C(CH₃)₂–CH₂CH₂–N(CO-O-)–(2-C(CH₃)₃-phenyl-4-OH))]phenyl | Mp. Salt: 211° C. Hydrochloride |
| 14 | HO-(3-phenyl)-CH(OH)-CH₂-NH-C(CH₃)₂-CH₂-N(CO-O-)-(2-C(CH₃)₃-phenyl) | Mp. Base: 140° C. Mp. Salt: 166° C. Fumarate |
| 15 | NH₂—SO₂, F-phenyl-CH(OH)-CH₂-NH-C(CH₃)₂-CH₂CH₂-N(CO-O-)-(2-C(CH₃)₃-phenyl-4-OH) | Mp. Salt: 192° C. Fumarate |
| 16 | NH₂—SO₂, F-phenyl-CH(OH)-CH₂-NH-C(CH₃)₂-CH₂CH₂-N(CO-O-)-(2-C(CH₃)₃-phenyl-4-OCH₃) | Mp. Salt: 197° C. Fumarate |
| 17 | F, HO-phenyl-CH(OH)-CH₂-NH-C(CH₃)₂-CH₂-CH₂-N(CO-O-)-(2-C(CH₃)₃-phenyl) | Mp. Salt: 194° C. Methanesulfonate |
| 18 | NHSO₂CH₃, HO-phenyl-CH(OH)-CH₂-NH-C(CH₃)₂-CH₂-CH₂-N(CO-O-CH₂-phenyl) | Mp. Base: 200° C. Mp. Salt: 180° C. Formate |

-continued

| Example | Compound | Characteristics |
|---|---|---|
| 19 | 2-Cl-C₆H₄-CH(OH)-CH₂-NH-C(CH₃)₂-CH₂-CH₂-N(COO-C(CH₃)₃)-C₆H₄-(2-) | Mp. Salt: 251° C. Hydrochloride |
| 20 | (3-NH₂SO₂, 4-F)-C₆H₃-CH(OH)-CH₂-NH-C(CH₃)₂-CH₂-CH₂-N(COO-C(CH₃)₃)-C₆H₄-(2-) | Mp. Salt: 235° C. Fumarate |
| 21 | 3-HO-C₆H₄-CH(OH)-CH₂-NH-C(CH₃)₂-CH₂-CH₂-N(COO-C(CH₃)₃)-C₆H₄-(2-) | Mp. Salt: 180° C. Formate |
| 22 | (3-CH₃O₂S-NH, 4-HO)-C₆H₃-CH(OH)-CH₂-NH-C(CH₃)₂-CH₂-CH₂-N(COO-CH(CH₂CH₃))-C₆H₄-(2-) | Mp. Salt: 182° C. Hydrochloride |
| 23 | (2-OCH₃, 4-CH₃)-C₆H₃-CH(OH)-CH₂-NH-C(CH₃)₂-CH₂-CH₂-N(COO-C(CH₃)₃)-C₆H₄-(2-) | Mp. Salt: 223° C. Hydrochloride |
| 24 | 3-HO-C₆H₄-CH(OH)-CH₂-NH-C(CH₃)₂-CH₂-CH₂-N(COO-CH(CH₃))-C₆H₄-(2-) | Mp. Salt: 153° C. Formate |
| 25 | (2-OCH₃, 4-CH₃)-C₆H₃-CH(OH)-CH₂-NH-C(CH₃)₂-CH₂-CH₂-N(COO-CH(CH₃))-C₆H₄-(2-) | Mp. Salt: 190° C. Hydrochloride |

-continued

| Example | Compound | Characteristics |
|---|---|---|
| 26 | CH₃—SO₂—NH, HO, CH(OH)—CH₂—NH—C(CH₃)₂—CH₂—CH₂—N(phenyl-2-isopropyl)(CO-O) | Mp. Salt: 192° C. Formate |
| 27 | HO-phenyl-CH(OH)—CH₂—NH—CH₂—CH₂—CH₂—N(phenyl-2-tert-butyl)(CO-O) | Mp. Salt: 147° C. Formate |
| 28 | CH₃—NH—OC, HO, CH(OH)—CH₂—NH—C(CH₃)₂—CH₂—CH₂—N(phenyl-2-(C(C₂H₅)₂))(CO-O) | Mp. Salt: 214° C. Methanesulfonate |
| 29 | H₂N—OC, HO, CH(OH)—CH₂—NH—C(CH₃)₂—CH₂—CH₂—N(phenyl-2-(C(C₂H₅)₂))(CO-O) | Mp. Base: 183° C. Mp. Salt: 208° C. Hydrochloride |
| 30 | (CH₃)₂CH—S-phenyl-CH(OH)—CH(CH₃)—NH—CH₂—CH₂—CH₂—N(phenyl-2-tert-butyl)(CO-O) | Mp. Salt: 153° C. Hydrochloride |
| 31 | CH₃—NH—OC, HO, CH(OH)—CH(CH₂CH₃)—NH—CH₂—CH₂—CH₂—N(phenyl-2-tert-butyl)(CO-O) | Mp. Salt: 165° C. Methanesulfonate |

-continued

| Example | Compound | Characteristics |
|---|---|---|
| 32 | CH₃—O₂S—NH, HO—C₆H₃—CH(OH)—CH(CH₂CH₃)—NH—CH₂CH₂CH₂—N(C₆H₄-o-C(CH₃)₃)—C(=O)—O— | Mp. Salt: 183° C. Succinate |
| 33 | CH₃—CO—O—C₆H₄—CH(OH)—CH₂—NH—C(CH₃)₂—CH₂CH₂—N(C₆H₄-o-C(CH₃)₃)—C(=O)—O— | Mp. Salt: 102° C. Formate |
| 34 | CH₃—SO₂NH, C₆H₅—CH₂—O—C₆H₃—CH(OH)—CH₂—NH—C(CH₃)₂—CH₂CH₂—N(C₆H₄-o-C(CH₃)₃)—C(=O)—O— | Mp. Salt: 162° C. Formate |
| 35 | C₆H₅—CH₂—O—C₆H₄—CH(OH)—CH₂—NH—C(CH₃)₂—CH₂CH₂—N(C₆H₄-o-C(CH₃)₃)—C(=O)—O— | Mp. Salt: 167° C. Fumarate |
| 36 | CH₃—O₂S—NH, C₆H₅—CH₂—O—C₆H₃—CH(OH)—CH₂—NH—C(CH₃)₂—CH₂CH₂—N(C₆H₄-o-CH(CH₃)—CH₂—CH₃)—C(=O)—O— | Mp. Salt: 137° C. Maleate |
| 37 | C₆H₅—CH₂—O—C₆H₄—CH(OH)—CH₂—NH—C(CH₃)₂—CH₂CH₂—N(C₆H₄-o-CH(CH₃)₂)—C(=O)—O— | Mp. Salt: 157° C. Fumarate |
| 38 | CH₃—O₂S—NH, C₆H₅—CH₂—O—C₆H₃—CH(OH)—CH(CH₂—CH₃)—NH—CH₂CH₂CH₂—N(C₆H₄-o-C(CH₃)₃)—C(=O)—O— | amorphous |

-continued

| Example | Compound | Characteristics |
|---|---|---|
| 39 | CH₃—SO₂—NH, C₆H₅—CH₂—O—C₆H₃—CH(OH)—CH₂—NH—C(CH₃)₂—CH₂—CH₂—N(C₆H₄-o-CH(CH₃)—O—CO—) | Mp. Salt: 166° C. Maleate |
| 40 | C₆H₅—CH₂—O—C₆H₄—CH(OH)—CH₂—NH—CH₂—CH₂—CH₂—N(C₆H₄-o-C(CH₃)₃ with cyclic —O—CO—) | Mp. Salt: 142° C. Hydrochloride |
| 41 | CH₃—SO₂—NH, C₆H₅—CH₂—O—C₆H₃—CH(OH)—CH₂—NH—C(CH₃)₂—CH₂—CH₂—N(C₆H₄-o-C(CH₃)₃, —O—CO—) | amorphous |
| 42 | CH₃—NH—OC, C₆H₅—CH₂—O—C₆H₃—CH(OH)—CH₂—NH—C(CH₃)₂—CH₂—CH₂—N(C₆H₄-o-CH(CH₂CH₃)—O—CO—) | amorphous |
| 43 | CH₃—SO₂—NH, C₆H₅—CH₂—O—C₆H₃—CH(OH)—CH₂—NH—C(CH₃)₂—CH₂—CH₂—N(C₆H₃-(OCH₃)(C(CH₃)₃)—O—CO—) | amorphous |
| 44 | CH₃—SO₂—NH, C₆H₅—CH₂—O—C₆H₃—CH(OH)—CH₂—NH—C(CH₃)₂—CH₂—CH₂—N(C₆H₃-(OH)(C(CH₃)₃)—O—CO—) | amorphous |

-continued

| Example | Compound | Characteristics |
|---|---|---|
| 45 | $C_6H_5-CH_2-O-\underset{OH}{C_6H_3}-\underset{OH}{CH}-CH_2-NH-\underset{CH_3}{\overset{CH_3}{C}}-CH_2-N(C_6H_4-C(CH_3)_3)-C(=O)-O$ | Mp. Salt: 173° C. Fumarate |
| 46 | $C_6H_5-CH_2-O-C_6H_3(F)-\underset{OH}{CH}-CH_2-NH-\underset{CH_3}{\overset{CH_3}{C}}-CH_2-CH_2-N(C_6H_4-C(CH_3)_3)-C(=O)-O$ | Mp. Salt: 192° C. Methanesulfonate |
| 47 | $CH_3-NH-OC$, $C_6H_5-CH_2-O-C_6H_3-\underset{OH}{CH}-CH_2-NH-\underset{CH_3}{\overset{CH_3}{C}}-CH_2-CH_2-N(C_6H_4-C(CH_3)_3)-C(=O)-O$ | Mp. Salt: 183° C. Methanesulfonate |
| 48 | $HO-CH_2-CH_2-NH-OC$, $C_6H_5-CH_2-O-C_6H_3-\underset{OH}{CH}-CH_2-NH-\underset{CH_3}{\overset{CH_3}{C}}-CH_2-CH_2-N(C_6H_4-C(CH_3)_3)-C(=O)-O$ | Mp. Salt: 170° C. Maleate |
| 49 | $CH_3-NH-OC$, $C_6H_5-CH_2-O-C_6H_3-\underset{OH}{CH}-\underset{CH_2-CH_3}{CH}-NH-CH_2-CH_2-CH_2-N(C_6H_4-C(CH_3)_3)-C(=O)-O$ | Mp. Salt: 142° C. Maleate |
| 50 | $CH_3-O_2S-NH$, $C_6H_5-CH_2-O-C_6H_3-\underset{OH}{CH}-CH_2-NH-\underset{CH_3}{\overset{CH_3}{C}}-CH_2-CH_2-N(C_6H_4-CH_2-)-C(=O)-O$ | Mp. Salt: 189° C. Maleate |
| 51 | $CH_3OOC$, $HO-C_6H_3-\underset{OH}{CH}-CH_2-NH-\underset{CH_3}{\overset{CH_3}{C}}-CH_2-CH_2-N(C_6H_4-CH(CH_3)-)-C(=O)-O$ | Mp. Salt: 155° C. p-Aminobenzoate |

| Example | Compound | Characteristics |
|---|---|---|
| 52 | CH₃OOC–[2-hydroxyphenyl]–CH(OH)–CH₂–NH–CH₂–CH₂–CH₂–N(2-tert-butylphenyl)–C(=O)–O | Mp. Salt: 191° C. Hydrochloride |
| 53 | CH₃OOC–[2-hydroxyphenyl]–CH(OH)–CH₂–NH–C(CH₃)₂–CH₂–N(2-tert-butylphenyl)–C(=O)–O | Mp. Salt: 153° C. p-Aminobenzoate |
| 54 | CH₃OOC–[2-hydroxyphenyl]–CH(OH)–CH₂–NH–C(CH₃)₂–CH₂–CH₂–N(2-(3-pentyl)phenyl)–C(=O)–O | Mp. Salt: 89° C. Maleate |
| 55 | CH₃OOC–[2-hydroxyphenyl]–CH(OH)–CH₂–NH–C(CH₃)₂–CH₂–CH₂–N(2-(1-propyl)phenyl)–C(=O)–O | Mp. Salt: 120° C. Maleate |
| 56 | C₆H₅–CH₂–O–[3-CH₃OOC-phenyl]–CH(OH)–CH(CH₂CH₃)–NH–CH₂–CH₂–CH₂–N(2-tert-butylphenyl)–C(=O)–O | Mp. Salt: 142° C. Maleate |
| 57 | CH₃OOC–[2-hydroxyphenyl]–CH(OH)–CH₂–NH–C(CH₃)₂–CH₂–CH₂–N(2-benzyl)–C(=O)–O | Mp. Salt: 188° C. p-Aminobenzoate |

| Example | Compound | Characteristics |
|---|---|---|
| 58 | ![Structure 58] CH₃—CH₂—NH—OC, HO, CH—CH₂—NH—C(CH₃)₂—CH₂—CH₂—N(—C(CH₃)₃-phenyl)(C(=O)O) with OH | Mp. Salt: 200° C. Methanesulfonate |
| 59 | HO—CH₂—CH₂—NH—OC, HO, CH—CH₂—NH—C(CH₃)₂—CH₂—CH₂—N(—C(CH₃)₃-phenyl)(C(=O)O) with OH | Mp. Base: 161° C. Mp. Salt: 181° C. Hydrochloride |
| 60 | Cl, H₂N, Cl—phenyl—CH(OH)—CH₂—NH—C(CH₃)₂—CH₂—CH₂—N(—C(CH₃)₃-phenyl)(C(=O)O) | Mp. Salt: 170° C. Maleate |
| 61 | O—CH₂—C₆H₅, O—CH₂—C₆H₅, CH₃-substituted phenyl—CH(OH)—CH₂—NH—C(CH₃)₂—CH₂—CH₂—N(—C(CH₃)₃-phenyl)(C(=O)O) | Mp. Salt: 212° C. Hydrochloride |
| 62 | O—CH₂—C₆H₅, O—CH₂—C₆H₅, O—CH₃-substituted phenyl—CH(OH)—CH₂—NH—C(CH₃)₂—CH₂—CH₂—N(—C(CH₃)₃-phenyl)(C(=O)O) | Mp. Salt: 195° C. Hydrochloride |

(EXAMPLES RELATING TO PROCESS STEP (B))

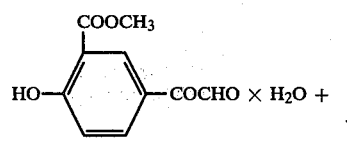

+

-continued

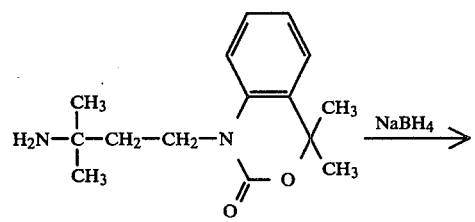

EXAMPLE 63

1-(3-Methoxycarbonyl-4-hydroxyphenyl)-2-{1,1-dimethyl-3-[1-(4,4-dimethyl-3,1-benzoxazin-2-onyl)]-propylamino}-ethanol

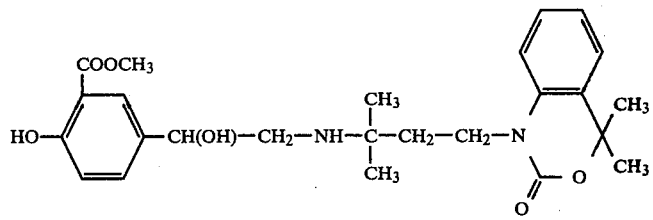

A mixture of 81.4 g of 3-methoxycarbonyl-4-hydroxyphenylglyoxal and 79 g of 1,1-dimethyl-3-[1-(4,4-dimethyl-3,1-benzoxazin-2-onyl)]-propylamine is heated to 50° C. in 1 liter of methanol, then kept at ambient temperature for 3 hours, after which 36 g of sodium borohydride are added in batches, with stirring, at −10° C. The reaction is completed by stirring at −5° to 0° C. for 3 hours. The mixture is acidified to pH 2 to 3 using 2 N hydrochloric acid, the solvent is distilled off in vacuo, concentrated ammonia solution is added to the residue to give a pH of 9 to 10, and the product is extracted three times with ethyl acetate. The combined ethyl acetate phases are dried over sodium sulphate and concentrated by evaporation. The residue contains 147 g of the title compound. In order to prepare the maleate, the residue is dissolved in 500 ml of acetonitrile and mixed with 34.8 g of maleic acid.

The maleate has a melting point of 139°–140° C.

The following are obtained analogously to Example 63 by using process step (b):

| Example | Compound | Characteristics |
|---|---|---|
| 64 | ![structure] CH₃—SO₂—NH / C₆H₅—CH₂—O—phenyl—CH(OH)—CH₂—NH—C(CH₃)₂—CH₂—CH₂—N(benzoxazinone) with OH on right phenyl | amorphous |
| 65 | C₆H₅—CH₂—O—phenyl—CH(OH)—CH₂—NH—C(CH₃)₂—CH₂—N(benzoxazinone) | Mp. Salt: 173° C. Fumarate |
| 66 | C₆H₅—CH₂—O—phenyl(F)—CH(OH)—CH₂—NH—C(CH₃)₂—CH₂—CH₂—N(benzoxazinone) | Mp. Salt: 192° C. Methanesulfonate |
| 67 | CH₃—NH—OC / C₆H₅—CH₂—O—phenyl—CH(OH)—CH₂—NH—C(CH₃)₂—CH₂—CH₂—N(benzoxazinone) | Mp. Salt: 183° C. Methanesulfonate |

-continued

| Example | Compound | Characteristics |
|---|---|---|
| 68 | HO—CH₂—CH₂—NH—OC— (on benzene ring with C₆H₅—CH₂—O—), —CH(OH)—CH₂—NH—C(CH₃)(CH₃)—CH₂—CH₂—N(—C₆H₄-o-C(CH₃)₃)—C(=O)—O— | Mp. Salt: 170° C. Maleate |
| 69 | CH₃—NH—OC— (on benzene ring with C₆H₅—CH₂—O—), —CH(OH)—CH(CH₂CH₃)—NH—CH₂—CH₂—CH₂—N(—C₆H₄-o-C(CH₃)₃)—C(=O)—O— | Mp. Salt: 142° C. Maleate |
| 70 | CH₃—O₂S—NH— (on benzene ring with C₆H₅—CH₂—O—), —CH(OH)—CH₂—NH—C(CH₃)(CH₃)—CH₂—CH₂—N(—C₆H₄-o-CH₂—)—C(=O)—O— | Mp. Salt: 189° C. Maleate |
| 71 | CH₃—SO₂—NH— (on benzene ring with C₆H₅—CH₂—O—), —CH(OH)—CH₂—NH—C(CH₃)(CH₃)—CH₂—CH₂—N(—C₆H₄-o-C(CH₃)₃)—C(=O)—O— | Mp. Salt: 162° C. Formate |
| 72 | C₆H₅—CH₂—O— (on benzene ring), —CH(OH)—CH₂—NH—C(CH₃)(CH₃)—CH₂—CH₂—N(—C₆H₄-o-C(CH₃)₃)—C(=O)—O— | Mp. Salt 167° C. Fumarate |
| 73 | CH₃—O₂S—NH— (on benzene ring with C₆H₅—CH₂—O—), —CH(OH)—CH₂—NH—C(CH₃)(CH₃)—CH₂—CH₂—N(—C₆H₄-o-CH(CH₃)—CH₂—CH₃)—C(=O)—O— | Mp. Salt: 137° C. Maleate |
| 74 | C₆H₅—CH₂—O— (on benzene ring), —CH(OH)—CH₂—NH—C(CH₃)(CH₃)—CH₂—CH₂—N(—C₆H₄-o-CH(CH₃)—)—C(=O)—O— | Mp. Salt: 157° C. Fumarate |

-continued

| Example | Compound | Characteristics |
|---|---|---|
| 75 | CH₃—O₂S—NH, C₆H₅—CH₂—O— phenyl —CH(OH)—CH(CH₂—CH₃)—NH—CH₂—CH₂—CH₂—N(phenyl-2-C(CH₃)₃)—C(=O)—O— | amorphous |
| 76 | CH₃—SO₂—NH, C₆H₅—CH₂—O— phenyl —CH(OH)—CH₂—NH—C(CH₃)₂—CH₂—CH₂—N(phenyl-2-CH(CH₃)—)—C(=O)—O— | Mp. Salt: 166° C. Maleate |
| 77 | C₆H₅—CH₂—O— phenyl —CH(OH)—CH₂—NH—CH₂—CH₂—CH₂—N(phenyl-2-C(CH₃)₃)—C(=O)—O— | Mp. Salt: 142° C. Hydrochloride |
| 78 | CH₃—SO₂—NH, C₆H₅—CH₂—O— phenyl —CH(OH)—CH₂—NH—C(CH₃)₂—CH₂—CH₂—N(phenyl-2-C(CH₃)₃)—C(=O)—O— | amorphous |
| 79 | CH₃—NH—OC, C₆H₅—CH₂—O— phenyl —CH(OH)—CH₂—NH—C(CH₃)₂—CH₂—CH₂—N(phenyl-2-CH₂—CH₃)—C(=O)—O— | amorphous |
| 80 | CH₃—SO₂—NH, C₆H₅—CH₂—O— phenyl —CH(OH)—CH₂—NH—C(CH₃)₂—CH₂—CH₂—N(phenyl-2-C(CH₃)₃, 4-OCH₃)—C(=O)—O— | amorphous |

-continued

| Example | Compound | Characteristics |
|---|---|---|
| 81 | (structure) | Mp. Base: 195° C.<br>Mp. Salt: 204° C.<br>Methanesulfonate |
| 82 | (structure) | Mp. Salt: 170° C.<br>Formate |
| 83 | (structure) | Mp. Salt: 143° C.<br>Formate |
| 84 | (structure) | Mp. Salt: 169° C.<br>Formate |
| 85 | (structure) | Mp. Base: 176° C.<br>Mp. Salt: 181° C.<br>Formate |
| 86 | (structure) | Mp. Salt: 210° C.<br>Hydrochloride |

-continued

| Example | Compound | Characteristics |
|---|---|---|
| 87 | CH₃—NH—OC, HO–[phenyl]–CH(OH)–CH₂–NH–C(CH₃)₂–CH₂–N(–[2-tert-butylphenyl])–C(=O)–O– (cyclic carbamate) | Mp. Salt: 165° C. p-Aminobenzoate |
| 88 | NH₂—OC, HO–[phenyl]–CH(OH)–CH₂–NH–C(CH₃)₂–CH₂–CH₂–N(–[2-tert-butylphenyl])–C(=O)–O– | Mp. Base: 197° C. Mp. Salt: 138° C. Methanesulfonate |
| 89 | NH₂—SO₂, F–[phenyl]–CH(OH)–CH₂–NH–C(CH₃)₂–CH₂–CH₂–N(–[2-tert-butylphenyl])–C(=O)–O– | Mp. Salt: 235° C. Fumarate |
| 90 | CH₃OOC, HO–[phenyl]–CH(OH)–CH₂–NH–C(CH₃)₂–CH₂–CH₂–N(–[2-isopropylphenyl])–C(=O)–O– | Mp. Salt: 155° C. p-Aminobenzoate |
| 91 | CH₃OOC, HO–[phenyl]–CH(OH)–CH₂–NH–CH₂–CH₂–CH₂–N(–[2-tert-butylphenyl])–C(=O)–O– | Mp. Salt: 191° C. Hydrochloride |
| 92 | CH₃OOC, HO–[phenyl]–CH(OH)–CH₂–NH–C(CH₃)₂–CH₂–N(–[2-tert-butylphenyl])–C(=O)–O– | Mp. Salt: 153° C. p-Aminobenzoate |
| 93 | OCH₃ on phenyl, CH₃–[phenyl]–CH(OH)–CH₂–NH–C(CH₃)₂–CH₂–CH₂–N(–[2-tert-butylphenyl])–C(=O)–O– | Mp. Salt: 223° C. Hydrochloride |

-continued

| Example | Compound | Characteristics |
|---|---|---|
| 94 | 2-chlorophenyl-CH(OH)-CH₂-NH-C(CH₃)₂-CH₂-CH₂-N(2-(C(CH₃)₃)phenyl)-C(=O)-O (cyclic carbamate) | Mp. Salt: 251° C. Hydrochloride |
| 95 | 3-(NH₂SO₂)-4-F-phenyl derivative with 4-OH-2-(C(CH₃)₃)phenyl carbamate | Mp. Salt: 192° C. Fumarate |
| 96 | 3-(NH₂SO₂)-4-F-phenyl derivative with 4-OCH₃-2-(C(CH₃)₃)phenyl carbamate | Mp. Salt: 197° C. Fumarate |
| 97 | 3-(CH₃OOC)-4-HO-phenyl-CH(OH)-CH₂-NH-C(CH₃)₂-CH₂-CH₂-N(2-(C(C₂H₅)₂)phenyl) carbamate | Mp. Salt: 89° C. Maleate |
| 98 | 3-(CH₃OOC)-4-HO-phenyl-CH(OH)-CH₂-NH-C(CH₃)₂-CH₂-CH₂-N(2-(CH(CH₂CH₃))phenyl) carbamate | Mp. Salt: 120° C. Maleate |
| 99 | 3-(CH₃OOC)-4-(C₆H₅-CH₂-O)-phenyl-CH(OH)-CH(CH₂CH₃)-NH-CH₂-CH₂-CH₂-N(2-(C(CH₃)₃)phenyl) carbamate | Mp. Salt: 142° C. Maleate |

| Example | Compound | Characteristics |
|---|---|---|
| 100 | ![structure] | Mp. Salt: 188° C. p-Aminobenzoate |
| 101 | ![structure] | Mp. Salt: 170° C. Maleate |
| 102 | ![structure] | Mp. Salt: 212° C. Hydrochloride |
| 103 | ![structure] | Mp. Salt: 195° C. Hydrochloride |

(EXAMPLES RELATING TO PROCESS STEP (C))

EXAMPLE 104

1-(3-Methylcarbamoyl-4-hydroxyphenyl)-2-{1,1-dimethyl-3-[1-(4,4-dimethyl-3,1-benzoxazin-2-onyl)]-propylamino}-ethanol

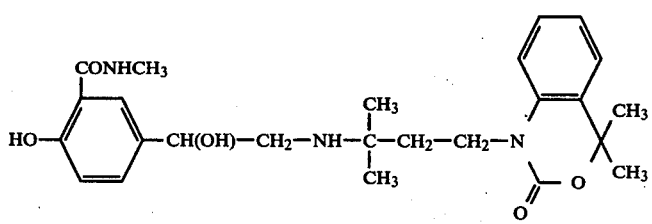

A solution of 5 g of 1-(3-methylcarbamoyl-4-benzyloxyphenyl)-2-{1,1-dimethyl-3-[1-(4,4-dimethyl-3,1-benzoxazin-2-onyl)]-propylamino-} ethanol in 50 ml of methanol is adjusted to pH 6.8 with about 2.2 ml of 13% methanolic hydrochloric acid and is hydrogenated at ambient temperature and under normal pressure in the presence of Pd/C as catalyst. After the catalyst has been removed by suction filtering, the title compound is precipitated as a base by adding methanolic methylamine solution (yield 94.7% of theory, m.p. 195° C.).

EXAMPLE 105

1-(3-Hydroxyphenyl)-2-{1,1-dimethyl-3-[1-(4,4-dimethyl-3,1-benzoxazin-2-onyl)]-propylamino}-ethanol

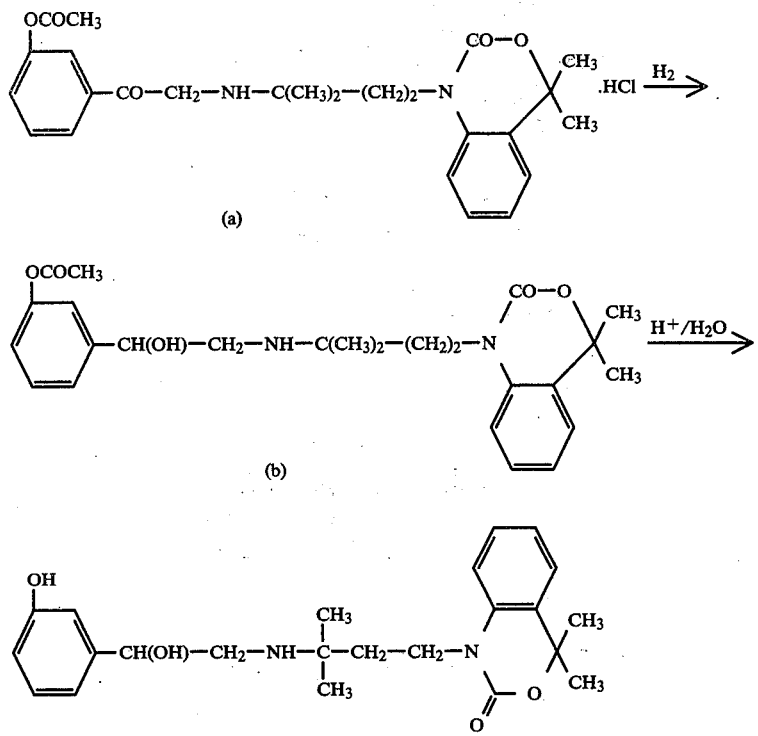

(a)

(b)

From the aminoketone hydrochloride (m.p. 195°–200° C.) of formula (a), the base is liberated with aqueous ammonia and is then isolated. For hydrogenation, 0.7 g of the base are used in the presence of 0.07 g of platinum oxide in 50 ml of methanol, at ambient temperature under normal pressure, to yield the corresponding amino alcohol of formula (b) (m.p. formate 102° C.). After the methanol has been distilled off, the residue is boiled with 2 ml of methanol and 2 ml of 1 N hydrochloric acid over a water bath for 30 minutes. The title compound produced is isolated as the formate (m.p. 180° C.) in a yield of 82% of theory.

The following are obtained analogously to Examples 104 and 105 by using process step (c):

| Example | Compound | Characteristics |
|---|---|---|
| 106 | ![compound 106] | Mp. Salt: 170° C. Formate |
| 107 | ![compound 107] | Mp. Salt: 143° C. Formate |

-continued

| Example | Compound | Characteristics |
|---|---|---|
| 108 | CH₃—NH—OC, HO, CH(OH)—CH₂—NH—CH₂—CH₂—CH₂—N(2-tert-butylphenyl)C(=O)O (cyclic carbamate) | Mp. Salt: 169° C. Formate |
| 109 | CH₃—NH—OC, HO, CH(OH)—CH₂—NH—C(CH₃)₂—CH₂—CH₂—N(2-tert-butyl-4-hydroxyphenyl)C(=O)O | Mp. Base: 176° C. Mp. Salt: 181° C. Formate |
| 110 | CH₃—NH—OC, HO, CH(OH)—CH₂—NH—C(CH₃)₂—CH₂—CH₂—N(2-tert-butyl-4-methoxyphenyl)C(=O)O | Mp. Salt: 210° C. Hydrochloride |
| 111 | CH₃—NH—OC, HO, CH(OH)—CH₂—NH—C(CH₃)₂—CH₂—N(2-tert-butylphenyl)C(=O)O | Mp. Salt: 165° C. p-Aminobenzoate |
| 112 | NH₂—OC, HO, CH(OH)—CH₂—NH—C(CH₃)₂—CH₂—CH₂—N(2-tert-butylphenyl)C(=O)O | Mp. Base: 197° C. Mp. Salt: 138° C. Methanesulfonate |
| 113 | CH₃—CH₂—NH—OC, HO, CH(OH)—CH₂—NH—C(CH₃)₂—CH₂—CH₂—N(2-tert-butylphenyl)C(=O)O | Mp. Salt: 200° C. Methanesulfonate |

-continued

| Example | Compound | Characteristics |
|---|---|---|
| 114 | HO—CH₂—CH₂—NH—OC-(4)-[HO(2)]-C₆H₃-CH(OH)-CH₂-NH-C(CH₃)₂-CH₂-CH₂-N(COO-)-C₆H₄-o-C(CH₃)₃ | Mp. Base: 161° C. Mp. Salt: 181° C. Hydrochloride |
| 115 | CH₃—SO₂—NH-(3)-[HO(2)]-C₆H₃-CH(OH)-CH₂-NH-C(CH₃)₂-CH₂-CH₂-N(COO-)-C₆H₄-o-C(CH₃)₃ | Mp. Salt: 164° C. Formate |
| 116 | CH₃—NH—OC-(4)-[HO(2)]-C₆H₃-CH(OH)-CH₂-NH-C(CH₃)₂-CH₂-CH₂-N(COO-)-C₆H₄-o-CH(CH₃)-CH₃ | Mp. Base: 163° C. Mp. Salt: 181° C. Hydrochloride |
| 117 | CH₃—SO₂—NH-(3)-[HO(2)]-C₆H₃-CH(OH)-CH₂-NH-C(CH₃)₂-CH₂-CH₂-N(COO-)-C₆H₃(4-OCH₃)-o-C(CH₃)₃ | Mp. Base: 181° C. Mp. Salt: 183° C. Hydrochloride |
| 118 | CH₃—SO₂—NH-(3)-[HO(2)]-C₆H₃-CH(OH)-CH₂-NH-C(CH₃)₂-CH₂-CH₂-N(COO-)-C₆H₃(4-OH)-o-C(CH₃)₃ | Mp. Salt: 211° C. Hydrochloride |
| 119 | HO-(3)-C₆H₄-CH(OH)-CH₂-NH-C(CH₃)₂-CH₂-N(COO-)-C₆H₄-o-C(CH₃)₃ | Mp. Base: 140° C. Mp. Salt: 166° C. Fumarate |

-continued

| Example | Compound | Characteristics |
|---|---|---|
| 120 | HO-C₆H₃(NHSO₂CH₃)-CH(OH)-CH₂-NH-C(CH₃)₂-CH₂-CH₂-N(benzyl-fused carbamate with 2-substituted phenyl) | Mp. Base: 200° C.<br>Mp. Salt: 180° C.<br>Formate |
| 121 | HO-C₆H₃(F)-CH(OH)-CH₂-NH-C(CH₃)₂-CH₂-CH₂-N(carbamate with 2-t-butylphenyl) | Mp. Salt: 194° C.<br>Methanesulfonate |
| 122 | CH₃-NH-OC-C₆H₃(OH)-CH(OH)-CH₂-NH-C(CH₃)₂-CH₂-CH₂-N(carbamate with 2-(3-pentyl)phenyl) | Mp. Salt: 214° C.<br>Methanesulfonate |
| 123 | H₂N-OC-C₆H₃(OH)-CH(OH)-CH₂-NH-C(CH₃)₂-CH₂-CH₂-N(carbamate with 2-(3-pentyl)phenyl) | Mp. Base: 183° C.<br>Mp. Salt: 208° C.<br>Hydrochloride |
| 124 | CH₃-SO₂-NH-C₆H₃(OH)-CH(OH)-CH₂-NH-C(CH₃)₂-CH₂-CH₂-N(carbamate with 2-t-butylphenyl) | Mp. Base: 192° C. |
| 125 | HO-C₆H₄-CH(OH)-CH₂-NH-C(CH₃)₂-CH₂-CH₂-N(carbamate with 2-t-butylphenyl) | Mp. Salt: 180° C.<br>Formate |
| 126 | CH₃-O₂S-NH-C₆H₃(OH)-CH(OH)-CH₂-NH-C(CH₃)₂-CH₂-CH₂-N(carbamate with 2-(1-propyl)phenyl) | Mp. Salt: 182° C.<br>Hydrochloride |

-continued
| Example | Compound | Characteristics |
|---|---|---|
| 127 | 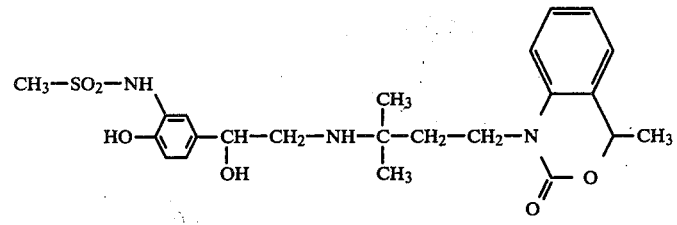 | Mp. Salt: 192° C.<br>Formate |
| 128 | 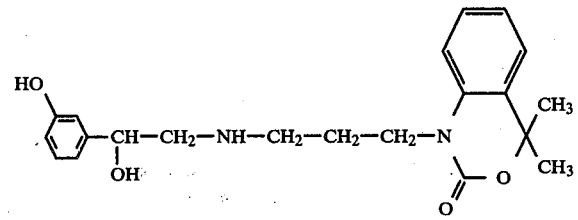 | Mp. Salt: 147° C.<br>Formate |
| 129 | 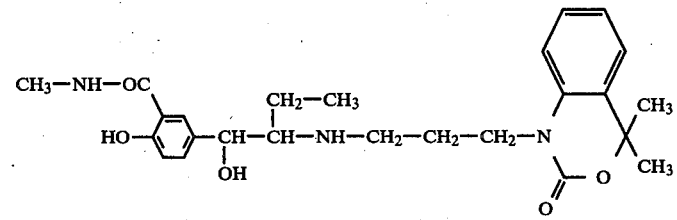 | Mp. Salt: 165° C.<br>Methanesulfonate |
| 130 | 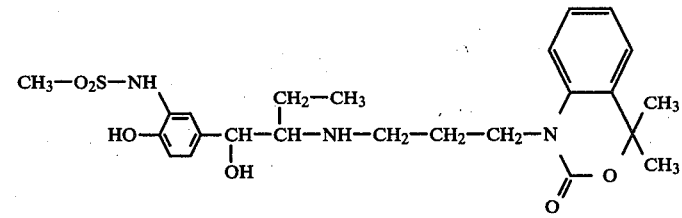 | Mp. Salt: 183° C.<br>Succinate |
| 131 | 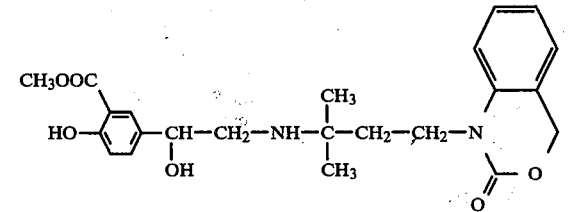 | Mp. Salt: 188° C.<br>p-Aminobenzoate |
| 132 | 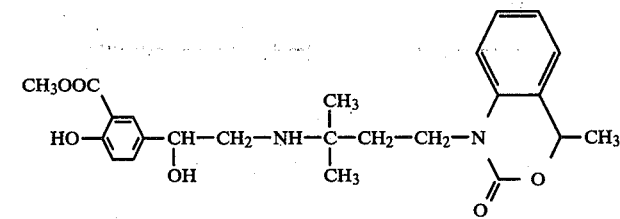 | Mp. Salt: 155° C.<br>p-Aminobenzoate |

-continued

| Example | Compound | Characteristics |
|---------|----------|-----------------|
| 133 | CH₃OOC—C₆H₃(OH)—CH(OH)—CH₂—NH—CH₂—CH₂—CH₂—N(C₆H₄-C(CH₃)₂CH₃)—C(O)—O | Mp. Salt: 191° C. Hydrochloride |
| 134 | CH₃OOC—C₆H₃(OH)—CH(OH)—CH₂—NH—C(CH₃)₂—CH₂—N(C₆H₄-C(CH₃)₂CH₃)—C(O)—O | Mp. Salt: 153° C. p-Aminobenzoate |
| 135 | CH₃OOC—C₆H₃(OH)—CH(OH)—CH₂—NH—C(CH₃)₂—CH₂—CH₂—N(C₆H₄-C(C₂H₅)₂)—C(O)—O | Mp. Salt: 89° C. Maleate |
| 136 | CH₃OOC—C₆H₃(OH)—CH(OH)—CH₂—NH—C(CH₃)₂—CH₂—CH₂—N(C₆H₄-CH(CH₂—CH₃))—C(O)—O | Mp. Salt: 120° C. Maleate |
| 137 | HO,CH₃—C₆H₂(OH)—CH(OH)—CH₂—NH—C(CH₃)₂—CH₂—CH₂—N(C₆H₄-C(CH₃)₂CH₃)—C(O)—O | Mp. Salt: 183° C. Formate |
| 138 | HO,O—CH₃—C₆H₂(OH)—CH(OH)—CH₂—NH—C(CH₃)₂—CH₂—CH₂—N(C₆H₄-C(CH₃)₂CH₃)—C(O)—O | Mp. Salt: 172° C. Formate |

EXAMPLES RELATING TO PROCESS STEP (D))

Example 139

1-(3-Methylcarbamoyl-4-hydroxyphenyl)-2-{1,1-dimethyl-3-[1-(4,4-dimethyl-3,1-benzoxazin-2-onyl)]-propylamino}-ethanol

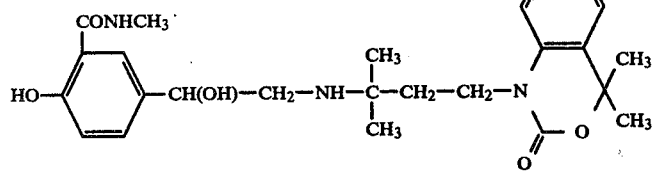

A mixture of 9.1 g of 1-(3-methoxycarbonyl-4-hydroxyphenyl)-2-{1,1-dimethyl-3-[1-(4,4-dimethyl-3,1-benzoxazin-2-onyl)]-propylamino}-ethanol and 10 ml of methylamine in 50 ml of methanol is reacted to yield the title compound by being left to stand for 4 days at ambient temperature. After the solvent has been distilled off, the title compound is isolated as the formate in acetonitrile as solvent (m.p. 174° C., yield 9.7 g).

The base (m.p. 194° C.) is obtained from the formate with aqueous ammonia solution.

The following are obtained analogously to Example 139 by using process step (d):

| Example | Compound | Characteristics |
|---|---|---|
| 140 | [structure] | Mp. Salt: 170° C. Formate |
| 141 | [structure] | Mp. Salt: 143° C. Formate |
| 142 | [structure] | Mp. Salt: 169° C. Formate |
| 143 | [structure] | Mp. Base: 176° C. Mp. Salt: 181° C. Formate |

-continued

| Example | Compound | Characteristics |
|---|---|---|
| 144 | CH₃—NH—OC—[4-OH, 3-position]—C₆H₃—CH(OH)—CH₂—NH—C(CH₃)₂—CH₂—CH₂—N(COO)—C₆H₃(t-Bu)(OCH₃) (cyclic carbamate) | Mp. Salt: 210° C. Hydrochloride |
| 145 | CH₃—NH—OC—[4-OH]—C₆H₃—CH(OH)—CH₂—NH—C(CH₃)₂—CH₂—N(COO)—C₆H₄(t-Bu) | Mp. Salt: 165° C. p-Aminobenzoate |
| 146 | NH₂—OC—[4-OH]—C₆H₃—CH(OH)—CH₂—NH—C(CH₃)₂—CH₂—CH₂—N(COO)—C₆H₄(t-Bu) | Mp. Base: 197° C. Mp. Salt: 138° C. Methanesulfonate |
| 147 | CH₃—CH₂—NH—OC—[4-OH]—C₆H₃—CH(OH)—CH₂—NH—C(CH₃)₂—CH₂—CH₂—N(COO)—C₆H₄(t-Bu) | Mp. Salt: 200° C. Methanesulfonate |
| 148 | HO—CH₂—CH₂—NH—OC—[4-OH]—C₆H₃—CH(OH)—CH₂—NH—C(CH₃)₂—CH₂—CH₂—N(COO)—C₆H₄(t-Bu) | Mp. Base: 161° C. Mp. Salt: 181° C. Hydrochloride |
| 149 | CH₃—NH—OC—[4-OH]—C₆H₃—CH(OH)—CH₂—NH—C(CH₃)₂—CH₂—CH₂—N(COO)—C₆H₄(C(C₂H₅)₂) | Mp. Salt: 214° C. Methanesulfonate |

-continued

| Example | Compound | Characteristics |
|---------|----------|-----------------|
| 150 | H₂N—OC, HO—[phenyl]—CH(OH)—CH₂—NH—C(CH₃)₂—CH₂—CH₂—N(—C(=O)O—)—[phenyl]—C(C₂H₅)₂—C₂H₅ | Mp. Base: 183° C.<br>Mp. Salt: 208° C.<br>Hydrochloride |
| 151 | CH₃—NH—OC, HO—[phenyl]—CH(OH)—CH₂—NH—C(CH₃)₂—CH₂—CH₂—N(—C(=O)O—)—[phenyl]—CH(CH₂—CH₃) | Mp. Base: 163° C.<br>Mp. Salt: 181° C.<br>Hydrochloride |
| 152 | CH₃—NH—O—C, C₆H₅—CH₂—O—[phenyl]—CH(OH)—CH₂—NH—C(CH₃)₂—CH₂—CH₂—N(—C(=O)O—)—[phenyl]—CH(CH₂—CH₃) | amorphous |
| 153 | CH₃—NH—OC, C₆H₅—CH₂—O—[phenyl]—CH(OH)—CH₂—NH—C(CH₃)₂—CH₂—CH₂—N(—C(=O)O—)—[phenyl]—C(CH₃)₂CH₃ | Mp. Salt: 183° C.<br>Methanesulfonate |
| 154 | HO—CH₂—CH₂—NH—OC, C₆H₅—CH₂—O—[phenyl]—CH(OH)—CH₂—NH—C(CH₃)₂—CH₂—CH₂—N(—C(=O)O—)—[phenyl]—C(CH₃)₂CH₃ | Mp. Salt: 170° C.<br>Maleate |
| 155 | CH₃—NH—OC, C₆H₅—CH₂—O—[phenyl]—CH(OH)—CH(CH₂—CH₃)—NH—CH₂—CH₂—CH₂—N(—C(=O)O—)—[phenyl]—C(CH₃)₂CH₃ | Mp. Salt: 142° C.<br>Maleate |

The following examples illustrate pharmaceutical compositions according to the invention:

EXAMPLE I

| Capsules |
|----------|
| Ingredients: |
| 1-(3-methylcarbamoyl-4-hydroxyphenyl)-2-{1,1-dimethyl-3-[1-(4,4-dimethyl-3,1-benzoxazin-2-onyl)]-propylamino}- ethanol- |

Capsules

| Ingredients: | |
|---|---|
| methanesulfonate | 100 mg |
| Corn starch | 300 mg |
| | 400 mg |

The ingredients are thoroughly mixed in the proportions stated and gelatine capsules are filled with 400 mg of the mixture.

EXAMPLE II

Tablets

| Ingredients: | |
|---|---|
| 1-(3-Methanesulfonamido-4-hydroxyphenyl)-2-{1,1-dimethyl-3-[1-(4-methyl-3,1-benzoxazin-2-onyl)]-propylamino}-ethanol-formate | 2 mg |
| Colloidal silicic acid | 10 mg |
| Lactose | 116 mg |
| Potato starch | 60 mg |
| Polyvinylpyrrolidone | 6 mg |
| Na-cellulose glycolate | 4 mg |
| Magnesium stearate | 2 mg |
| | 200 mg |

The ingredients are processed in the usual way to form tablets weighing 200 mg, each containing 2 mg of active substance. Instead of the compound mentioned, 1-(3-methanesulfonamido-4-hydroxyphenyl)-2-{1,1-dimethyl-3-[1-(4-methyl-3,1-benzoxazin-2-onyl)]-propylamino}-ethanol-formate, it is also be possible to use other compounds according to the invention.

EXAMPLE III

Ampoules

| Composition of the solution: | |
|---|---|
| Active substance according to the invention | 2 mg |
| Sorbitol | 40 mg |
| Distilled water ad | 10 ml |

The active substance and the sorbitol are dissolved in sufficient distilled water and made up to the required volume with distilled water. The solution is filled into ampoules in the conventional way.

EXAMPLE IV

Capsules containing powder for inhalation

Each hard gelatine capsule is filled with a mixture of 0.5 mg of an active substance according to the invention e.g. 1-(3-methanesulfonamido-4-hydroxyphenyl)-2-{1,1-dimethyl-3-[1-(4,4-dimethyl-6-hydroxy-3,1-benzoxazin-2-onyl)]-propylamino}-ethanol-hydrochloride, and 19.5 mg of lactose with a particle diameter of between 0.5 and 7 μm.

The active substances according to the invention may also be combined with known active substances; for broncholytic application, for example, they may be combined with theophyllines, parasympatholytics (e.g. ipratropium bromide), secretolytics (e.g. bromhexine), musculotropic spasmolytics (e.g. papaverine), corticoids and antiallergic agents.

For use as uterine relaxants, the compounds may be combined with corticoids and, for reducing blood pressure, they may be combined with saluretics and other antihypertensive agents.

We claim:

1. A compound of the formula

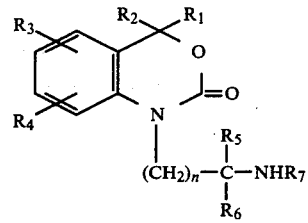

wherein
$R_1$ and $R_2$ are each hydrogen or alkyl of 1 to 4 carbon atoms;
$R_3$ and $R_4$ are each hydrogen, fluorine, chlorine, hydroxyl, methyl, ethyl or alkoxy of 1 to 4 carbon atoms; or
$R_3$ and $R_4$, together with each other are methylenedioxy;
$R_5$ and $R_6$ are each hydrogen or methyl;
$R_7$ is

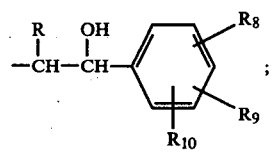

R is hydrogen or alkyl of 1 to 4 carbon atoms;
$R_8$ is fluorine, chlorine, alkyl of 1 to 4 carbon atoms, (alkyl of 1 to 4 carbon atoms)thio, hydroxymethyl, $-CONHR_{11}$, $-SO_2NHR_{11}$, $-OR_{12}$, methoxycarbonyl, ethoxycarbonyl or $-NHSO_2CH_3$;
$R_9$ is hydrogen, fluorine, chlorine or $-OR_{12}$;
$R_{10}$ is hydrogen, chlorine, amino, methyl or methoxy;
$R_{11}$ is hydrogen, methyl, ethyl or hydroxyethyl;
$R_{12}$ is hydrogen, alkyl of 1 to 4 carbon atoms, (alkyl of 1 to 4 carbon atoms)carbonyl, aryl—$CH_2$— or arylcarbonyl; and
n is 1, 2 or 3;
or a non-toxic, pharmacologically acceptable acid addition salt thereof.

2. A compound of claim 1, where
$R_1$ and $R_2$ are each methyl or one of them is methyl and the other is hydrogen;
$R_3$ is hydrogen, hydroxyl or methoxy;
$R_4$ is hydrogen;
$R_5$ and $R_6$ are each hydrogen or methyl;
$R_7$ is

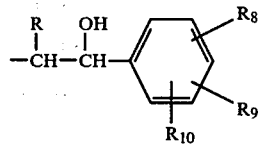

R is hydrogen, methyl or ethyl;
$R_8$ is $-CONHR_{11}$, $-SO_2NHR_{11}$, $-NHSO_2CH_3$, $OR_{12}$, fluorine, chlorine, methoxycarbonyl, ethoxycarbonyl or hydroxymethyl;
$R_9$ is $-OR_{12}$, fluorine or chlorine;
$R_{10}$ is hydrogen, amino, methyl, methoxy or chlorine;

$R_{11}$ is hydrogen, methyl or ethyl;

$R_{12}$ is hydrogen, aryl—$CH_2$— or (alkyl of 1 to 4 carbon atoms)-carbonyl; and n is 1 or 2;

or a non-toxic, pharmacologically acceptable acid addition salt thereof.

3. A compound of claim 1, selected from the group consisting of 1-(3-methoxycarbamoyl-4-hydroxy-phenyl)-2-{1,1-dimethyl-3-[1-(4,4-dimethyl-3,1-benzoxazin-2-onyl)]-propylamino=ethanol;

1-(3-methanolsulfonamido-4-hydroxy-phenyl)-2-{1,1-dimethyl-3-[1-(4-methyl-3,1-benzoxazin-2-onyl)]-propylamino}ethanol;

1-(3-methanesulfonamido-4-hydroxy-phenyl)-2-{1,1-dimethyl-3-[1-(4,4-dimethyl-6-hydroxy-3,1-benzoxazin-2-onyl)]-propylamino}ethanol;

1-(3-methanesulfonamido-4-hydroxy-phenyl)-2-{1,1-dimethyl-3-[1-(4,4-dimethyl-3,1-benzoxazin-2-onyl)]-propylamino}ethanol;

1-(3-methoxycarbonyl-4-hydroxy-phenyl)-2-{1,1-dimethyl-3-[1-(4,4-dimethyl-3,1-benzoxazin-2-onyl)]-propylamino}-ethanol;

1-(3-hydroxy-phenyl)-2-{1,1-dimethyl-3-[1-(4,4-dimethyl-3,1-benzoxazin-2-onyl)]propylamino}ethanol; and non-toxic, pharmacologically acceptable acid addition salts thereof.

4. A hypotensive or tocolytic pharmaceutical composition consisting essentially of an inert pharmaceutical carrier and an effective hypotensive or tocolytic amount of a compound of claim 1.

5. The method of lowering the blood pressure or suppressing uterine contractions in a warm-blooded animal in need thereof, which comprises perorally or parenterally administering to said animal an effective hypotensive or tocolytic amount of a compound of claim 1.

* * * * *